United States Patent
Inoue et al.

(10) Patent No.: US 8,784,958 B2
(45) Date of Patent: Jul. 22, 2014

(54) MULTILAYER FILM AND CONTAINER

(75) Inventors: Fujio Inoue, Naruto (JP); Isamu Tateishi, Naruto (JP); Yasushi Morimoto, Naruto (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 788 days.

(21) Appl. No.: 12/528,305

(22) PCT Filed: Feb. 18, 2008

(86) PCT No.: PCT/JP2008/052668
§ 371 (c)(1),
(2), (4) Date: Feb. 23, 2010

(87) PCT Pub. No.: WO2008/102733
PCT Pub. Date: Aug. 28, 2008

(65) Prior Publication Data
US 2010/0143627 A1    Jun. 10, 2010

(30) Foreign Application Priority Data
Feb. 23, 2007 (JP) ................ 2007-044067

(51) Int. Cl.
*B32B 1/02* (2006.01)
*B32B 1/08* (2006.01)

(52) U.S. Cl.
USPC ....... 428/35.7; 428/34.1; 428/34.2; 428/35.9; 428/36.9; 428/516

(58) Field of Classification Search
USPC ............. 428/34.1, 34.2, 35.7, 35.9, 36.9, 516
See application file for complete search history.

(56) References Cited

U.S. PATENT DOCUMENTS

| | | | |
|---|---|---|---|
| 5,783,269 A | 7/1998 | Heilmann et al. | |
| 5,912,070 A | 6/1999 | Milharu et al. | |
| 6,319,991 B1 * | 11/2001 | Okayama et al. | 525/240 |
| 6,503,993 B1 * | 1/2003 | Huovinen et al. | 526/348.1 |
| 6,849,313 B2 * | 2/2005 | Mechelaere et al. | 428/35.2 |
| 2008/0063825 A1 | 3/2008 | Mori et al. | |

FOREIGN PATENT DOCUMENTS

| | | |
|---|---|---|
| JP | 10-045978 | 2/1998 |
| JP | 3155924 | 2/2001 |
| JP | 2002-301796 | 10/2002 |

(Continued)

OTHER PUBLICATIONS

Supplementary European Search Report dated Jul. 29, 2011.

*Primary Examiner* — Marc Patterson
(74) *Attorney, Agent, or Firm* — Finnegan, Henderson, Farabow, Garrett & Dunner, L.L.P.

(57) ABSTRACT

In a multilayer film including a first layer (1), a second layer (2), a third layer (3), a fourth layer (4) and a fifth layer (5) stacked in this order, the first layer (1) is composed of a propylene-ethylene random copolymer and/or a polypropylene homopolymer, and the second layer (2) and the fourth layer (4) are each composed of a mixture of a propylene-ethylene random copolymer and an α-olefin elastomer. The third layer (3) is composed of a mixture of a polycycloolefin and polyethylene, and the fifth layer (5) is composed of a mixture containing a polypropylene homopolymer and a propylene-ethylene random copolymer in a weight ratio of 90:10 to 10:90. A container is formed of the multilayer film with an outer layer and an inner layer thereof being defined by the first layer (1) and the fifth layer (5), respectively.

7 Claims, 2 Drawing Sheets

(56) References Cited

FOREIGN PATENT DOCUMENTS

| | | |
|---|---|---|
| JP | 2004-121824 | 4/2004 |
| JP | 2006-021504 | 1/2006 |
| JP | 2006-224482 | 8/2006 |
| TW | 349058 | 1/1999 |
| WO | WO 2006/043459 | 4/2006 |

\* cited by examiner

MULTILAYER FILM AND CONTAINER

TECHNICAL FIELD

The present invention relates to a multilayer film and a container and, more specifically, to a multilayer film and a container for containing a drug solution, blood or the like for use in medical applications.

BACKGROUND ART

Conventionally, multilayer films of polyolefin resins such as polypropylene and polyethylene are widely used for formation of medical containers such as infusion solution bags.

In recent years, multi-chamber containers in which a plurality of substances can be separately contained and mixed with each other for use are widely employed in the field of medical containers. For such a multi-chamber container, it is important to properly control the unsealability of a weakly sealed portion which isolates adjacent chambers from each other.

Therefore, the multilayer film has a layered structure designed in consideration of the unsealability, the transparency, the mechanical strength, the sterilization heat resistance and other properties of the film and the prevention of exudation of additives from the film into a liquid contained in the container (contamination resistance).

In Patent Document 1, a multilayer film and a drug solution bag formed of this multilayer film are disclosed. The multilayer film includes an innermost first layer of a polypropylene and an ethylene-propylene copolymer, a second layer of a modified polyolefin, a third layer of an ethylene-vinyl alcohol copolymer, a fourth layer of a modified polyolefin, and an outermost fifth layer of an ethylene-propylene copolymer or of a polypropylene and an ethylene-propylene copolymer.

Further, a flexible plastic film and a container formed of the flexible plastic film are disclosed in Patent Document 2. The flexible plastic film includes a heat-sealable sealing layer, a first soft layer provided on a surface of the sealing layer, a reinforcement layer provided on a surface of the first soft layer, a second soft layer provided on a surface of the reinforcement layer, and an outermost layer provided on a surface of the second soft layer. The sealing layer is composed of a mixture of a propylene-α-olefin random copolymer having a crystal melting point of 135 to 145° C. and a polypropylene homopolymer having a crystal melting point higher than 160° C., and the first and second soft layers are each composed of a mixture of a propylene-α-olefin random copolymer and an ethylene-α-olefin copolymer elastomer. The reinforcement layer is composed of at least one polymer selected from the group consisting of a polypropylene homopolymer, a propylene-α-olefin random copolymer and a polycycloolefin, and the outermost layer is composed of at least one polymer selected from the group consisting of a polypropylene homopolymer and a propylene-α-olefin random copolymer.

A five-layer film and a container formed of the five-layer film are disclosed in Patent Document 3. The five-layer film includes a first layer and a fifth layer each composed of a linear ethylene-α-olefin copolymer having a density of 0.930 to 0.950 g/cm$^3$, a second layer and a fourth layer each composed of a very low density linear ethylene-α-olefin copolymer alone prepared by employing a metallocene catalyst and having a density of 0.860 to 0.920 g/cm$^3$ or of a resin mixture containing a very low density linear ethylene-α-olefin copolymer prepared by employing a metallocene catalyst and having a density of 0.860 to 0.920 g/cm$^3$ and not greater than 10% by weight of a high density polyethylene having a density of 0.955 to 0.970 g/cm$^3$, and a third layer composed of a cycloolefin copolymer.

Patent Document 1: JP-A-2006-224482
Patent Document 2: JP-A-2006-21504
Patent Document 3: JP-A-2002-301796

DISCLOSURE OF THE INVENTION

Problems to be Solved by the Invention

The container formed of the multilayer film disclosed in Patent Document 1 is problematic in that, where a drug solution containing an antibiotic or the like is contained in the container, for example, additives added to the resin of the multilayer film are liable to exude into the drug solution (the multilayer film has a lower contamination resistance).

In the case of the containers each formed of the multilayer film including an intermediate layer composed of the cyclic olefin (cycloolefin) polymer or copolymer (hereinafter referred to generally as "polycycloolefin") as disclosed in Patent Documents 2 and 3, the exudation of the additives into the drug solution from the multilayer film is suppressed.

In recent years, however, it is desirable to impart a multilayer film having a polycycloolefin intermediate layer and a container formed of the multilayer film with properties superior to those of the multilayer films and the containers disclosed in Patent Documents 2 and 3.

It is therefore an object of the present invention to provide a multilayer film and a container formed of the multilayer film, which are excellent in unsealability, transparency, mechanical strength and sterilization heat resistance and are capable of preventing exudation of additives from the film into a liquid contained in the container.

Means for Solving the Problems

To achieve the aforementioned object, a multilayer film according to the present invention comprises a first layer, a second layer provided on the first layer, a third layer provided on the second layer, a fourth layer provided on the third layer, and a fifth layer provided on the fourth layer, the first layer comprising a propylene-ethylene random copolymer and/or a polypropylene homopolymer, the second layer and the fourth layer each comprising a mixture of a propylene-ethylene random copolymer and an α-olefin elastomer, the third layer comprising a mixture of a polycycloolefin and a polyethylene, the fifth layer comprising a mixture containing a polypropylene homopolymer and a propylene-ethylene random copolymer in a weight ratio of 90:10 to 10:90.

In the inventive multilayer film, the mixture of the polycycloolefin and the polyethylene is employed as a material for the third layer, which serves as a middle layer of the multilayer film. Therefore, it is possible to suppress exudation of additives from the multilayer film into a drug solution in contact with the fifth layer (inner layer) of the multilayer film. In addition, penetration of moisture (particularly, steam) through the multilayer film is suppressed, because the third layer contains the polycycloolefin.

Not only the polycycloolefin but also the polyethylene is employed in the form of a mixture as the material for the third layer (middle layer). Therefore, the multilayer film is excellent in adhesive strength (interlayer strength) between the third layer and the second and fourth layers adjacent to the third layer, so that a container to be described later is imparted with excellent mechanical strength (e.g., impact strength).

In the multilayer film, the propylene-ethylene random copolymer and/or the polypropylene homopolymer are employed as a material for the first layer, which serves as an outer layer where the container is formed of the multilayer film. Therefore, the multilayer film is excellent in processability when the container is produced from the multilayer film, and degradation of the multilayer film is suppressed when a peripheral portion and a weakly sealed portion of the container are formed by heat-sealing the multilayer film.

In the multilayer film, the mixture containing the polypropylene homopolymer and the propylene-ethylene random copolymer having different melting points in the aforementioned ratio is employed as a material for the fifth layer, which serves as an inner layer where the container is formed of the multilayer film. Therefore, a weakly sealed portion having excellent unsealability can be formed by utilizing a difference in melting point.

In the multilayer film, the mixture of the propylene-ethylene random copolymer and the α-olefin elastomer is employed as a material for the second layer (outer intermediate layer) provided between the first layer (outer layer) and the third layer (middle layer) and the fourth layer (inner intermediate layer) provided between the fifth layer (inner layer) and the third layer. Therefore, the multilayer film is excellent in adhesive strength (interlayer strength) between the third layer and the second and fourth layers and in mechanical strength, so that the container to be described later is imparted with excellent mechanical strength (e.g., impact strength).

The multilayer film is excellent in transparency, mechanical strength such as interlayer strength, and resistance to heat to be applied to the film for high-temperature sterilization such as steam sterilization and hot water sterilization.

In the inventive multilayer film, it is preferred that the mixture for the third layer contains the polycycloolefin in a proportion of 50 to 95% by weight based on the total weight thereof, and/or that the mixture for the second layer and the fourth layer contains the α-olefin elastomer in a proportion of 30 to 60% by weight based on the total weight thereof.

According to this preferred embodiment, the adhesive strength (interlayer strength) between the third layer (middle layer) and the second and fourth layers (outer and inner intermediate layers) adjacent to the third layer is further improved, so that the container to be described later is imparted with more excellent mechanical strength.

In the inventive multilayer film, it is preferred that the propylene-ethylene random copolymer contained in the second layer and the fourth layer is a mixture of a propylene-ethylene random copolymer having a melt flow rate not less than 0.5 g/10 minutes and less than 5 g/10 minutes as measured at 230° C. and a propylene-ethylene random copolymer having a melt flow rate (g/10 minutes) not less than 5 g/10 minutes and not greater than 10 g/10 minutes as measured at 230° C.

This preferred embodiment improves the strength of the multilayer film, while ensuring proper moldability and transparency of the multilayer film.

In the inventive multilayer film, it is preferred that the thickness of the second layer is not less than 0.8 times the thickness of the fourth layer. In this case, it is more preferred that the thickness of the second layer is not greater than 1.2 times the thickness of the fourth layer.

This preferred embodiment further improves the effect of suppressing the exudation of the additives into the drug solution in contact with the fifth layer (inner layer), while ensuring the multilayer film mechanical strength improving effect provided by the second layer and the fourth layer.

In the inventive multilayer film, it is preferred that a total thickness of the second layer and the fourth layer is not less than 50% of the thickness of the multilayer film.

This preferred embodiment further improves the mechanical strength of the multilayer film, and imparts the container to be described later with more excellent mechanical strength.

An inventive container is formed of the multilayer film with an outer layer and an inner layer thereof being defined by the first layer and the fifth layer, respectively.

That is, the inventive container is formed of a multilayer film including a first layer, a second layer provided on the first layer, a third layer provided on the second layer, a fourth layer provided on the third layer, and a fifth layer provided on the fourth layer, the first layer comprising a propylene-ethylene random copolymer and/or a polypropylene homopolymer, the second layer and the fourth layer each comprising a mixture of a propylene-ethylene random copolymer and an α-olefin elastomer, the third layer comprising a mixture of a polycycloolefin and a polyethylene, the fifth layer comprising a mixture containing a polypropylene homopolymer and a propylene-ethylene random copolymer in a weight ratio of 90:10 to 10:90, the first layer and the fifth layer respectively serving as an outer layer and an inner layer of the container.

Since the inventive container is formed of the multilayer film as described above, the container can be formed with a weakly sealed portion having excellent unsealability. The inventive container is excellent in transparency, interlayer strength, impact strength (e.g., plate drop strength) and other mechanical strength, and resistance to heat to be applied to the container for high-temperature sterilization such as steam sterilization and hot water sterilization. Further, it is possible to suppress the exudation of the additives from the multilayer film into the drug solution contained in the container.

Effects of the Invention

The multilayer film and the container formed of the multilayer film according to the present invention are excellent in unsealability, transparency, mechanical strength and sterilization heat resistance, and are capable of suppressing the exudation of the additives from the multilayer film into the liquid contained in the container. The multilayer film and the container according to the present invention are suitable for medical containers such as infusion solution bags and, particularly, for containers containing antibiotics and containers to be subjected to a high-temperature sterilization process.

DESCRIPTION OF REFERENCE CHARACTERS

1: First layer, 2: Second layer, 3: Third layer, 4: Fourth layer, 5: Fifth layer, 6: Container (single-chamber bag), 10: Container (multi-chamber bag)

EMBODIMENTS OF THE INVENTION

Figure 1:
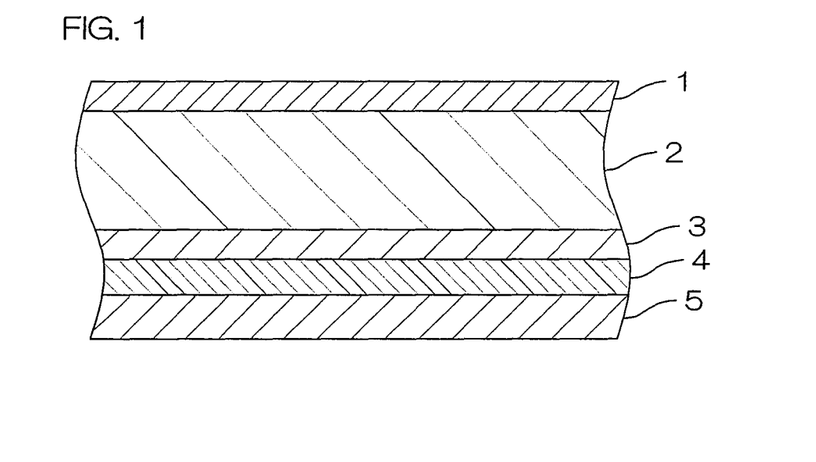
FIG. 1 is a schematic diagram showing the layered structure of a multilayer film according to the present invention.

FIG. 1 is a schematic diagram showing the layered structure of a multilayer film according to the present invention.

Figure 2:
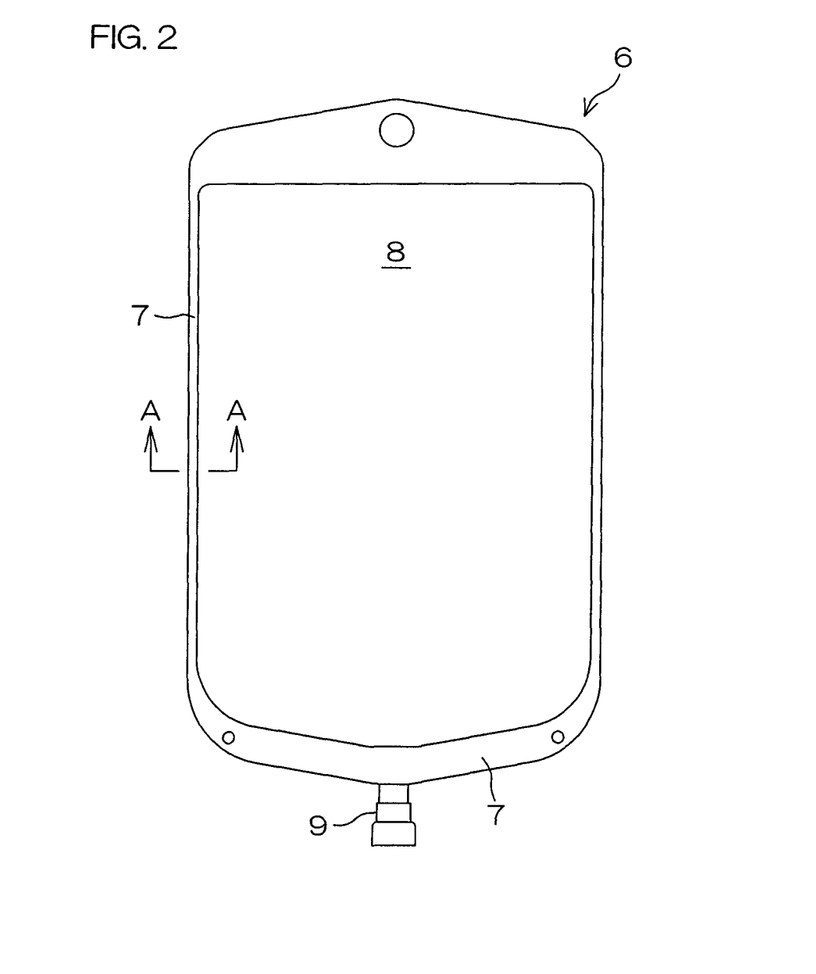
FIG. 2 is a front view illustrating a container according to one embodiment of the present invention.
Figure 3:
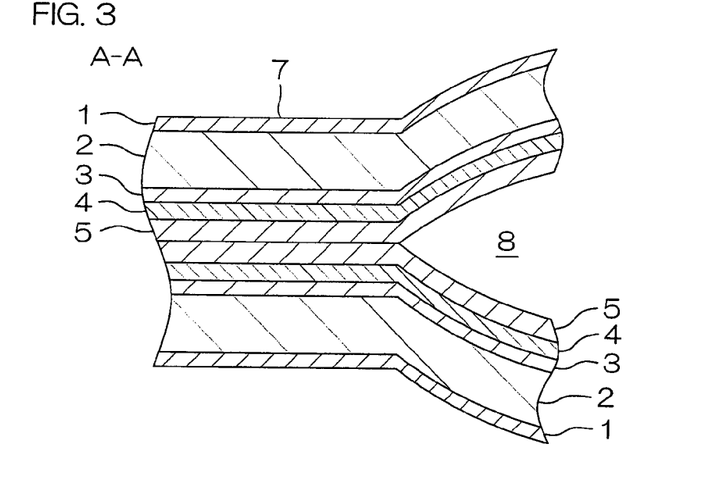
FIG. 3 is a schematic sectional view showing an A-A section in FIG. 2.
Figure 4:
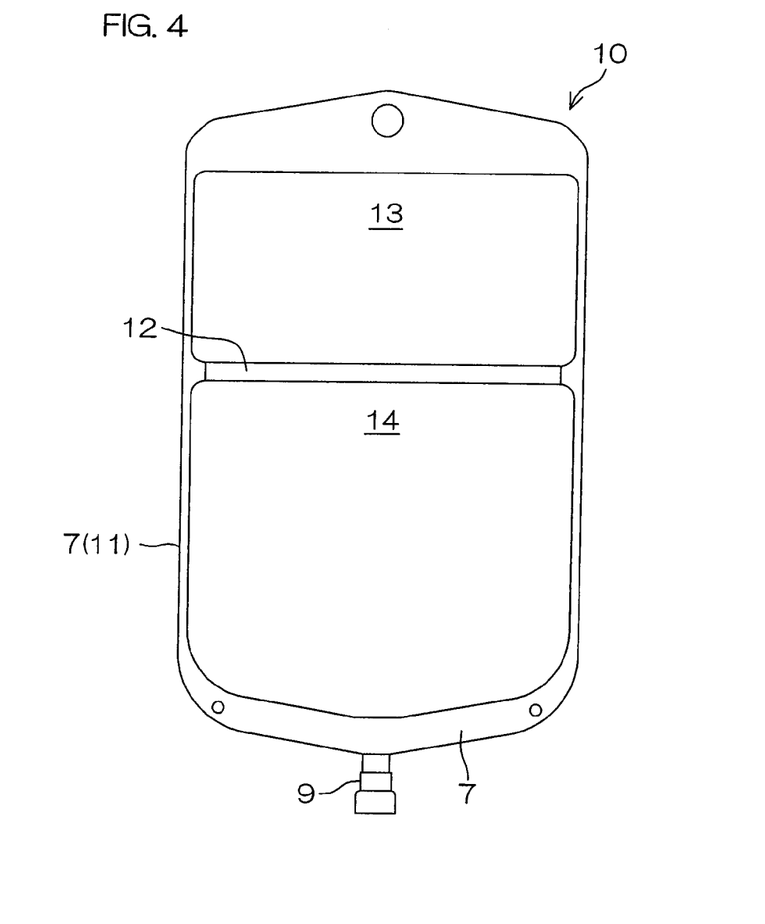
FIG. 4 is a front view illustrating a container according to another embodiment of the present invention.

FIG. 2 is a front view illustrating a container according to one embodiment of the present invention, and FIG. 3 is a schematic sectional view showing a portion A-A of the multilayer film in FIG. 2. FIG. 4 is a front view illustrating a container according to another embodiment of the present invention.

First, the inventive multilayer film will hereinafter be described with reference to FIG. 1.

Referring to FIG. 1, the multi layer film includes a first layer 1, a second layer 2 provided on the first layer 1, a third layer 3 provided on the second layer 2, a fourth layer 4 provided on the third layer 3, and a fifth layer 5 provided on the fourth layer 4.

The first layer 1 is located in one surface of the multilayer film, and serves as an outer layer of a container to be described later.

The first layer 1 is composed of a propylene-ethylene random copolymer and/or a polypropylene homopolymer. That is, the first layer 1 is composed of the propylene-ethylene random copolymer or the polypropylene homopolymer, or is composed of a mixture of the propylene-ethylene random copolymer and the polypropylene polymer.

The propylene-ethylene random copolymer and the polypropylene homopolymer may each be a single type of such a (co)polymer, or may each be a mixture of two or more types of such (co)polymers which are classified in the same category but are different in melting point, melt flow rate, density and other physical properties.

Where the transparency is important as a property of the multilayer film, it is preferred, but not limitative, that the propylene-ethylene random copolymer is used alone or the proportion of the propylene-ethylene random copolymer in the mixture is increased. Where the heat resistance is important, it is preferred, but not limitative, that the polypropylene homopolymer is used alone or the proportion of the polypropylene homopolymer in the mixture is increased.

Since the propylene-ethylene random copolymer and/or the polypropylene homopolymer are employed as a material for the first layer 1, the multilayer film is excellent in processability when a container is produced from the multilayer film, and deterioration of the multilayer film is suppressed which may otherwise occur when a peripheral portion and a weakly sealed portion of the container are formed by heat-sealing the film.

The propylene-ethylene random copolymer contains propylene unit recurring blocks and ethylene unit recurring blocks which are arranged at random. The ethylene content of the propylene-ethylene random copolymer is not particularly limited, but is preferably 1 to 5% by mole based on the amount of the propylene-ethylene random copolymer.

The melting point Tm of the propylene-ethylene random copolymer is not particularly limited, but is preferably 130 to 145° C., more preferably 135 to 140° C., as measured in conformity with ASTM D790.

The melt flow rate (MFR as measured in conformity with ASTM D1238) of the propylene-ethylene random copolymer is not particularly limited, but is preferably 0.5 to 10 g/10 minutes (at 230° C.), more preferably 3 to 8 g/10 minutes (at 230° C.).

A commercially available propylene-ethylene random copolymer may be used. Specific examples of the commercially available propylene-ethylene random copolymer include PRIME POLYPRO (trade name) series F327, B241 and B205 of a random copolymer grade available from Prime Polymer Co., Ltd.

The polypropylene homopolymer may be an isotactic polypropylene, a syndiotactic polypropylene or an atactic polypropylene, but is preferably the isotactic polypropylene or the syndiotactic polypropylene.

The melting point Tm of the polypropylene homopolymer is not particularly limited, but is preferably 160 to 164° C., more preferably 160 to 163° C., as measured in conformity with ASTM D790.

The melt flow rate (MFR as measured in conformity with ASTM D1238) of the polypropylene homopolymer is not particularly limited, but is preferably 0.5 to 5 g/10 minutes (at 230° C.), more preferably 1 to 4 g/10 minutes (at 230° C.).

A commercially available polypropylene homopolymer may be used. Specific examples of the commercially available polypropylene homopolymer include PRIME POLYPRO (trade name) series J104WT, J103 and J102 of a homopolymer grade available from Prime Polymer Co., Ltd.

For the first layer 1, another polymer may be mixed with the propylene-ethylene random copolymer and/or the polypropylene homopolymer. For example, the first layer 1 may contain an α-olefin elastomer or the like to impart the multilayer film with desired flexibility.

Exemplary α-olefins for the α-olefin elastomer include α-olefins having 3 to 12 carbon atoms, such as propylene, 1-butene, 1-pentene, 1-hexene, 4-methyl-1-pentene, 1-heptene, 1-octene, 1-nonene, 1-decene, 1-undecene and 1-dodecene, which may be used either alone or in combination. Preferably, propylene is employed as the α-olefin.

The α-olefin elastomer is generally available in the form of an ethylene-α-olefin elastomer.

The proportion of the α-olefin elastomer in the first layer 1 is not particularly limited, but is preferably not greater than 30% by weight, more preferably not greater than 10% by weight, based on the weight of the first layer 1.

The thickness of the first layer 1 is preferably 5 to 15%, more preferably 6 to 12%, of the thickness of the multilayer film.

The second layer 2 is located between the first layer 1 and the third layer 3 to be described later, and serves as an outer intermediate layer of the container to be described later.

The second layer 2 is composed of a mixture of a propylene-ethylene random copolymer and an α-olefin elastomer.

The propylene-ethylene random copolymer and the α-olefin elastomer may each be a single type of such a copolymer or an elastomer, or may each be a mixture of two or more types of such copolymers or elastomers which are classified in the same category but are different in melting point, melt flow rate, density and other physical properties.

Since the mixture of the propylene-ethylene random copolymer and the α-olefin elastomer is employed as a material for the second layer 2, the multilayer film is excellent in adhesive strength (interlayer strength) between the second layer 2 and the third layer 3 and in mechanical strength. Therefore, a container to be described later is imparted with excellent mechanical strength (e.g., impact strength).

The propylene-ethylene random copolymer has an ethylene content and a melting point Tm which are equivalent to those of the propylene-ethylene random copolymer described with respect to the first layer 1. A commercially available propylene-ethylene random copolymer may be used. Examples of the commercially available propylene-ethylene random copolymer include those described above.

The propylene-ethylene random copolymer to be used for the second layer 2 is preferably a mixture of two types of propylene-ethylene random copolymers having different MFRs. More specifically, the propylene-ethylene random copolymer is preferably a mixture of a propylene-ethylene random copolymer (low-MFR propylene-ethylene random copolymer) having a melt flow rate not less than 0.5 g/10 minutes and less than 5 g/10 minutes as measured at 230° C. and a propylene-ethylene random copolymer (high-MFR propylene-ethylene random copolymer) having a melt flow rate not less than 5 g/10 minutes and not greater than 10 g/10 minutes as measured at 230° C.

The high-MFR propylene-ethylene random copolymer tends to reduce the strength of the second layer 2, but is excellent in transparency and moldability. The MFR of the high-MFR propylene-ethylene random copolymer is particularly preferably 6 to 8 g/10 minutes (at 230° C.) in the aforesaid range.

On the other hand, the low-MFR propylene-ethylene random copolymer tends to reduce the transparency and the moldability of the second layer 2 as compared with the high-MFR propylene-ethylene random copolymer, but has the effect of improving the strength of the second layer 2. The MFR of the low-MFR propylene-ethylene random copolymer is particularly preferably 0.5 to 3 g/10 minutes (at 230° C.) in the aforesaid range.

Where the propylene-ethylene random copolymer to be used for the second layer 2 is a mixture of the high-MFR propylene-ethylene random copolymer and the low-MFR propylene-ethylene random copolymer, the content rate of the high-MFR propylene-ethylene random copolymer and the low-MFR propylene-ethylene random copolymer is preferably 40:60 to 70:30, more preferably 45:55 to 60:40, and is particularly preferably 1:1.

Exemplary α-olefins for the α-olefin elastomer include those described above, among which propylene and 1-butene are preferred, and 1-butene is more preferred.

The density of the α-olefin elastomer is not particularly limited, but is preferably 0.880 to 0.910 g/cm$^3$, more preferably 0.880 to 0.900 g/cm$^3$ as measured in conformity with ASTM D1505.

The melt flow rate (MFR as measured in conformity with ASTM D1238) of the α-olefin elastomer is not particularly limited, but is preferably 0.5 to 6 g/10 minutes (at 190° C.), more preferably 0.5 to 3 g/10 minutes (190° C.).

A commercially available α-olefin elastomer may be used. Specific examples of the commercially available α-olefin elastomer include TOUGHMER (registered trade mark) series A0585 and the like available from Mitsui Chemicals, Inc.

A mixing ratio between the propylene-ethylene random copolymer and the α-olefin elastomer is properly determined, for example, in consideration of the mechanical strength of the multilayer film, the mechanical strength of the container formed of the multilayer film and the adhesion between the second layer 2 and the third layer 3. The proportion of the α-olefin elastomer is preferably 30 to 60% by weight, more preferably 40 to 50% by weight, based on the weight of the mixture for the second layer 2.

For the second layer 2, another polymer may be mixed with the propylene-ethylene random copolymer and the α-olefin elastomer.

The thickness of the second layer 2 is properly determined in consideration of the mechanical strength of the multilayer film and the mechanical strength of the container formed of the multilayer film. For example, the thickness of the second layer 2 is preferably 30 to 60%, more preferably 40 to 50%, of the thickness of the multilayer film.

Further, the thickness of the second layer 2 is preferably 0.8 to 5 times, more preferably 0.8 to 1.2 times, the thickness of the fourth layer 4 to be described later, and is particularly preferably equal to the thickness of the fourth layer 4 in order to reduce the amount of the α-olefin copolymer in the fourth layer 4 to be described later and suppress the exudation of the additives into the drug solution in contact with the fifth layer 5 while ensuring the mechanical strength of the multilayer film and the mechanical strength of the container formed of the multilayer film.

The third layer 3 is opposed to the first layer 1 with the intervention of the second layer 2, and serves as a middle layer of the container to be described later.

The third layer 3 is composed of a mixture of a polycycloolefin and a polyethylene.

The polycycloolefin is a cycloolefin-containing polymer (cycloolefin polymer (COP)) or a cycloolefin-containing copolymer (cycloolefin copolymer (COC)).

The polycycloolefin may be a single type of such a (co) polymer, or may be a mixture of two or more types of such (co)polymers which are classified in the same category but are different in melting point, melt flow rate, density and the like.

Since the mixture of the polycycloolefin and the polyethylene is employed as a material for the third layer 3, penetration of moisture (particularly, steam) through the multilayer film is suppressed. In addition, the multilayer film is excellent in adhesive strength (interlayer strength) between the third layer 3 and the second and fourth layers 2, 4 and in mechanical strength. Therefore, the container to be described later is imparted with excellent mechanical strength (e.g., impact strength).

Examples of the cycloolefin polymer (COP) include ring-opening polymers of a cyclopentadiene compound, ring-opening polymers of a dicyclopentadiene compound and ring-opening polymers of a norbornene compound, and hydrogenation products of these ring-opening polymers.

An example of the cyclopentadiene compound is cyclopentadiene.

Examples of the dicyclopentadiene compound include dicyclopentadiene and 2,3-dihydrodicyclopentadiene.

Examples of the norbornene compound include 2-norbornene, 5-methyl-2-norbornene, 5,5-dimethyl-2-norbornene, 5-ethyl-2-norbornene, 5-butyl-2-norbornene and 5-ethylidene-2-norbornene.

Examples of the cycloolefin copolymer (COC) include: ring-opening copolymers of two or more types of cyclopentadiene compounds, ring-opening copolymers of two or more types of dicyclopentadiene compounds and ring-opening copolymers of two or more types of norbornene compounds, and hydrogenation products of these ring-opening copolymers; ring-opening copolymers of at least two cycloolefins selected from the group consisting of a cyclopentadiene compound, a dicyclopentadiene compound and a norbornene compound, and hydrogenation products of these ring-opening copolymers; and copolymers of a linear olefin and at least one cycloolefin selected from the group consisting of a cyclopentadiene compound, a dicyclopentadiene compound and a norbornene compound, and hydrogenation products of these copolymers.

Examples of the cyclopentadiene compound, the dicyclopentadiene compound and the norbornene compound for the copolymers include those described above.

Examples of the linear olefin for the copolymers include ethylene and α-olefins. Examples of the α-olefins include those described above. The linear olefin is preferably ethylene. These linear olefins may be used either alone or in combination.

The glass transition temperature Tg of the polycycloolefin is not particularly limited, but is preferably not lower than 70° C., more preferably 80 to 150° C. as measured in conformity with JIS K7121.

The molecular weight of the polycycloolefin is not particularly limited, but the number average molecular weight Mn of the polycycloolefin is preferably 10,000 to 100,000, more preferably 20,000 to 50,000, as measured by a gel permeation chromatography (GPC) analysis using cyclohexane as a solvent.

Where unsaturated bonds present in a molecular chain of the polycycloolefin is saturated by hydrogenation, the hydrogenation ratio is not particularly limited, but is preferably not less than 90%, more preferably not less than 95%, furthermore preferably 99% to 100%.

A commercially available polycycloolefin may be used. Specific examples of the commercially available polycycloolefin include APEL (registered trade mark) series APL6011T and APL6013T available from Mitsui Chemicals, Inc., ZEONOR (registered trade mark) series 1020R and 750R available from Nippon Zeon Corporation, and TOPAS (trade name) series available from Ticona GmbH.

Examples of the polyethylene include a high-density polyethylene (HDPE), a low-density polyethylene (LDPE) produced by a high pressure method, and a linear low-density polyethylene (LLDPE).

Any of the aforementioned polyethylenes may be employed, but a linear polyethylene is preferred in consideration of the transparency of the multilayer film, and a linear polyethylene having a density of 0.930 to 0.965 g/cm$^3$ as measured in conformity with ASTM D1505 is more preferred.

Further, an ethylene-α-olefin copolymer may be used as the polyethylene. In this case, exemplary α-olefins for the ethylene-α-olefin copolymer include those described above.

The polyethylene may be a single type of such a polymer, or may be a mixture of two or more types of such polymers which are classified in the same category but are different in melting point, melt flow rate, density, molecular chain structure, production method and the like.

The melt flow rate (MFR as measured in conformity with ASTM D1238) of the polyethylene is not particularly limited, but is preferably 0.5 to 20 g/10 minutes (at 190° C.), more preferably 1 to 10 g/10 minutes (at 190° C.).

The melting point $T_m$ of the polyethylene is not particularly limited, but is preferably 120 to 135° C., more preferably 122 to 131° C., as measured in conformity with ASTM D2117.

A commercially available polyethylene may be used. Specific examples of the commercially available polyethylene include ULTZEX (registered trade mark) series UZ4020B available from Prime Polymer Co., Ltd., and NEOZEX (registered trade mark) series NZ65150 available from Prime Polymer Co., Ltd.

A mixing ratio between the polycycloolefin and the polyethylene is properly determined, for example, in consideration of penetration of moisture (particularly, steam) through the multilayer film, resistance to contamination of the drug solution in contact with the fifth layer (inner layer) 5 (the effect of suppressing the exudation of the additives), the adhesive strength (interlayer strength) between the third layer and the second and fourth layers 2, 4, and the mechanical strength of the multilayer film. The proportion of the polycycloolefin is preferably 50 to 95% by weight, more preferably 70 to 90% by weight, based on the weight of the mixture for the third layer 3.

For the third layer 3, another polymer may be mixed with the polycycloolefin and the polyethylene. For example, the third layer 3 may contain an α-olefin elastomer or the like to impart the multilayer film with desired flexibility and provide sufficient adhesion to the second layer 2 and the fourth layer 4 to be described later. Examples of the α-olefin elastomer include those described above.

The proportion of the α-olefin elastomer in the third layer 3 is not particularly limited, but is preferably not greater than 30% by weight, more preferably not greater than 10% by weight, based on the weight of the third layer 3.

The thickness of the third layer 3 is preferably 5 to 15%, more preferably 6 to 12%, of the thickness of the multilayer film.

The fourth layer 4 is opposed to the second layer 2 with the intervention of the third layer 3, and serves as an inner intermediate layer of the container to be described later.

Like the second layer 2, the fourth layer 4 is composed of a mixture of a propylene-ethylene random copolymer and an α-olefin elastomer.

Since the mixture of the propylene-ethylene random copolymer and the α-olefin elastomer is employed as a material for the fourth layer 4, the multilayer film is excellent in adhesive strength (interlayer strength) between the fourth layer 4 and the third layer 3 and in the mechanical strength. Therefore, the container to be described later is imparted with excellent mechanical strength (e.g., impact strength).

The types, the physical properties and their preferable ranges, and the commercially available product names of the propylene-ethylene random copolymer and the α-olefin elastomer are the same as those of the propylene-ethylene random copolymer and the α-olefin elastomer employed for the second layer 2.

Where the propylene-ethylene random copolymer to be used for the fourth layer 4 is a mixture of the high-MFR propylene-ethylene random copolymer and the low-MFR propylene-ethylene random copolymer, both content rate of the high-MFR propylene-ethylene random copolymer and the low-MFR propylene-ethylene random copolymer is the same as those of the content rate for the second layer 2.

A mixing ratio between the propylene-ethylene random copolymer and the α-olefin elastomer is properly determined, for example, in consideration of the mechanical strength of the multilayer film, the mechanical strength of the container formed of the multilayer layer, and adhesion between the fourth layer 4 and the third layer 3. The proportion of the α-olefin elastomer is preferably 30 to 60% by weight, more preferably 40 to 50% by weight, based on the weight of the mixture for the fourth layer 4.

The thickness of the fourth layer 4 is properly determined in consideration of the mechanical strength of the multilayer film and the mechanical strength of the container formed of the multilayer film. For example, the thickness ratio of the fourth layer 4 to the multilayer film is equivalent to that of the second layer 2.

Further, the thickness of the fourth layer 4 is preferably 0.2 to 1.25 times, more preferably ⅝ to 1.25 times, the thickness of the second layer 2, and is particularly preferably equal to the thickness of the fourth layer 4 in order to reduce the amount of the α-olefin copolymer in the fourth layer 4 and suppress the exudation of the additives into the drug solution in contact with the fifth layer 5 while ensuring the mechanical strength of the multilayer film and the mechanical strength of the container formed of the multilayer film.

With the thickness ratio between the second layer 2 and the fourth layer 4 specified as described above, it is possible to suppress the exudation of the additives from the multilayer film into the drug solution in contact with the fifth layer (inner layer) 5 to be described later, while ensuring the mechanical strength of the multilayer film and the mechanical strength of the container formed of the multilayer film.

The total thickness of the second layer 2 and the fourth layer 4 is preferably not less than 50%, more preferably 50 to 70%, of the thickness of the multilayer film in order to improve the mechanical strength of the multilayer film and the mechanical strength of the container formed of the multilayer film.

The fifth layer 5 is located in the other surface of the multilayer film, and serves as an inner layer of the container to be described later.

The fifth layer 5 is composed of a mixture of a polypropylene homopolymer and a propylene-ethylene random copolymer.

The polypropylene homopolymer and the propylene-ethylene random copolymer may each be a single type of such a (co)polymer, or may each be a mixture of two or more types of such (co)polymers which are classified in the same category but are different in melting point, melt flow rate, density and other physical properties.

Since the mixture of the polypropylene homopolymer and the propylene-ethylene random copolymer is employed as a material for the fifth layer 5, the multilayer film can be formed with a weakly sealed portion having excellent unsealability by utilizing a difference in melting point between the polypropylene homopolymer and the propylene-ethylene random copolymer.

The types, the physical properties and the commercially available product names of the polypropylene homopolymer and the propylene-ethylene random copolymer are the same as those of the polypropylene homopolymer and the propylene-ethylene random copolymer described above.

A mixing ratio between the polypropylene homopolymer and the propylene-ethylene random copolymer is properly determined, for example, in consideration of the unsealability of the weakly sealed portion in the production of the container by employing the multilayer film. More specifically, the weight ratio between the polypropylene homopolymer and the propylene-ethylene random copolymer is typically 90:10 to 10:90, preferably 80:20 to 20:80, more preferably 70:30 to 40:60.

For the fifth layer 5, another polymer may be mixed with the polypropylene homopolymer and the propylene-ethylene random copolymer. For example, the fifth layer 5 may contain an α-olefin elastomer to impart the multilayer film with desired flexibility, sealability for the formation of the peripheral portion (heavily sealed portion) of the container to be described later, and unsealability for the formation of the weakly sealed portion of the container. Examples of the α-olefin elastomer include those described above.

The proportion of the α-olefin elastomer in the fifth layer 5 is not particularly limited, but is preferably not greater than 30% by weight, more preferably not greater than 10% by weight, based on the weight of the fifth layer 5.

The thickness of the fifth layer 5 is preferably 5 to 20%, more preferably 10 to 20%, of the thickness of the multilayer film.

The thickness of the multilayer film is not particularly limited, but is properly determined depending on the use and application of the multilayer film. Where the multilayer film is used as a material for an infusion solution bag (having a volume up to about 500 mL), a blood bag, an enteral nutrition bag, a fluid diet bag and other medical containers, the thickness of the multilayer film is generally 100 to 300 μm, preferably 100 to 220 μm, more preferably 160 to 200 μm.

A production method for the multilayer film is not particularly limited, but exemplary methods include a water-cooling or air-cooling co-extrusion inflation method, a co-extrusion T-die method, a dry lamination method and an extrusion lamination method, among which the water-cooling co-extrusion inflation method and the co-extrusion T-die method are preferred in consideration of the properties of the multilayer film, particularly, the transparency of the multilayer film, the economy of the production of the multilayer film and the cleanliness of the multilayer film.

In any of the aforementioned methods, the production of the multilayer film is carried out at a temperature at which the resins for the respective layers are meltable. If the temperature for the production is too high, the resins will be partly thermally decomposed, resulting in deterioration of the properties of the multilayer film due to presence of decomposition products. Therefore, the temperature for the production of the multilayer film is preferably 150 to 250° C., more preferably 170 to 200° C., but not limited thereto. Further, differences in MFR between the resins for the respective layers are preferably as small as possible for the transparency of the multilayer film.

The above-mentioned multilayer film is excellent in unsealability, transparency, mechanical strength, sterilization heat resistance, and resistance to contamination of the drug solution in contact with the fifth layer (inner layer) 5 (the effect of suppressing the exudation of the additives). Therefore, the multilayer film is suitable as a material for medical containers such as infusion solution bags.

Referring to FIGS. 2 and 3, a container 6 is formed of the multilayer film shown in FIG. 1 with an outer layer and an inner layer thereof being defined by the first layer 1 and the fifth layer 5, respectively.

The container 6 includes a sealed portion 7 which is formed by fusion-bonding peripheral edge portions of two multilayer films stacked one on the other with their fifth layers 5 opposed to each other. The sealed portion 7 may be formed by forming the multilayer film in a bag shape or a tube shape with its fifth layer 5 facing inward by an inflation method, and fusion-bonding a peripheral edge portion of the bag-shaped or tube-shaped multilayer film.

The container 6 has a container portion 8 defined by the sealed portion 7. The container 6 is a single-chamber bag which has the single container portion 8 therein.

A tube member 9 which permits a drug solution to flow into and out of the container portion 8 of the container 6 is interposed between the two multilayer films and fusion-bonded to a part of the sealed portion 7.

Conditions for the formation of the sealed portion 7 are not particularly limited, but a sealing temperature is typically 120 to 160° C. Where the multilayer films each have a thickness of about 180 μm, for example, a sealing period of 0.5 to 5 seconds may be employed for the formation of the sealed portion 7 at a temperature in the aforesaid range.

Referring to FIG. 4, a container 10 is formed of the multilayer film shown in FIG. 1 with an outer layer and an inner layer thereof being defined by the first layer 1 and the fifth layer 5, respectively.

The container 10 shown in FIG. 4 includes a sealed portion 11 which is formed by fusion-bonding peripheral edge portions of two multilayer films stacked one on the other with their fifth layers 5 opposed to each other, and a tube member 9 interposed between the two multilayer films and fusion-bonded to a part of the sealed portion 11.

The sealed portion 11 is equivalent to the sealed portion 7 of the container 6 shown in FIG. 2. Therefore, the sealed portion 11 is formed under the same conditions as described above.

The container 10 is a multi-chamber bag (multi-chamber container) having two container portions 13, 14 which respectively contain drug solutions. The two container portions 13, 14 are isolated from each other by an unsealable weakly sealed portion 12.

The weakly sealed portion 12 is formed by fusion-bonding the fifth layers 5 of the two multilayer films, and the sealing strength of the weakly sealed portion 12 is set such that the weakly sealed portion 12 can be easily unsealed when one of the two container portions 13, 14 is pressed to apply a liquid pressure to the weakly sealed portion 12 from the one container portion.

Heat-sealing conditions for the formation of the weakly sealed portion 12 are not particularly limited, but a sealing temperature is typically 110 to 130° C. Where the multilayer films each have a thickness of about 180 μm, for example, a sealing period of 0.5 to 5 seconds may be employed for the formation of the weakly sealed portion 12 at a temperature in the aforesaid range.

The tube member 9 is not particularly limited, but a known tube member may be employed. For example, the tube member 9 is a member which permits the drug solution contained in the container portion 8, 13, 14 of the container 6, 10 to flow out of the container 6, and permits a drug solution to flow into the container portion 8, 13, 14 from the outside of the container 6, 10. A sealing member (e.g., a rubber plug or the like) which seals the tube member 9 and is to be pierced by a hollow needle is typically provided in the tube member 9.

A method for filling the drug solution or the like in the container portion and sealing the container is not particularly limited, but a known method may be employed.

Since the container is formed of the inventive multilayer film with the outer layer and the inner layer thereof being defined by the first layer and the fifth layer, respectively, the container is excellent in unsealability, transparency, mechanical strength, sterilization heat resistance and resistance to contamination of the drug solution in contact with the fifth layer (inner layer) (the effect of suppressing the exudation of the additives).

Therefore, the container is advantageously used as a medical container such as an infusion solution bag. Further, where the container is the multi-chamber container, the container is advantageously used as an infusion solution bag which separately contains and stores two or more types of infusion solutions to be mixed for use, for example, as an antibiotic kit which separately contains and stores an antibiotic and a solvent for the antibiotic.

EXAMPLES

The present invention will hereinafter be described by way of examples thereof and comparative examples. However, it should be understood that the invention be not limited to the following examples.

Designations and properties of ingredients employed for multilayer films in the following examples and comparative examples will be first described.

R-PP1: A propylene-ethylene random copolymer having a melting point Tm of 137° C. (ASTM D790), a density of 0.90 g/cm$^3$ (ASTM D1505) and a melt flow rate (MFR) of 7.0 g/10 minutes (at 230° C.) (ASTM D1238), and available under the trade name of PRIME POLYPRO F327 from Prime Polymer Co., Ltd.

R-PP2: A propylene-ethylene random copolymer having a melting point Tm of 139° C. (ASTM D790), a density of 0.90 g/cm$^3$ (ASTM D1505) and an MFR of 0.5 g/10 minutes (at 230° C.) (ASTM D1238), and available under the trade name of PRIME POLYPRO B241 from Prime Polymer Co., Ltd.

R-PP3: A propylene-ethylene random copolymer having a melting point Tm of 155° C. (ASTM D790), a density of 0.910 g/cm$^3$ (ASTM D1505) and an MFR of 1.0 g/10 minutes (at 230° C.) (ASTM D1238), and available under the trade name of PRIME POLYPRO B205 from Prime Polymer Co., Ltd.

H-PP: A polypropylene homopolymer having a melting point Tm of 162° C. (ASTM D790), a density of 0.91 g/cm$^3$ (ASTM D1505) and an MFR of 3.2 g/10 minutes (at 230° C.) (ASTM D1238), and available under the trade name of PRIME POLYPRO J104WT from Prime Polymer Co., Ltd.

PE: A linear low density polyethylene having a density of 0.94 g/cm$^3$ (ASTM D1505) and an MFR of 2.1 g/10 minutes (at 190° C.) (ASTM D1238), and available under the trade name of ULTZEX (registered trade mark) 4020B from Prime Polymer Co., Ltd.

α-OE1: An α-olefin elastomer (adhesive polyolefin) having a melting point Tm of 71° C., a density of 0.885 g/cm$^3$ (ASTM D1505) and an MFR of 0.5 g/10 minutes (at 190° C.) (ASTM D1238), and available under the trade name of TOUGHMER (registered trade mark) A0585T from Mitsui Chemicals, Inc.

α-OE2: An α-olefin elastomer (adhesive polyolefin) having a melting point Tm of 71° C., a density of 0.885 g/cm$^3$ (ASTM D1505) and an MFR of 4.0 g/10 minutes (at 190° C.) (ASTM D1238), and available under the trade name of TOUGHMER (registered trade mark) A4085 from Mitsui Chemicals, Inc.

COP: A polycycloolefin (cycloolefin polymer) having a glass transition temperature Tg of 105° C. (JIS K7121), a specific gravity of 1.01 (ASTM D792), and available under the trade name of ZEONOR (registered trade mark) 1020R from Nippon Zeon Corporation Production of Multilayer Films and Containers Example 1

A multilayer film having a layered structure as shown in FIG. 1 and a thickness of 180 μm was produced by a water-cooling co-extrusion inflation method. Ingredients for the respective layers are shown in Table 1. In the "First layer (outer layer)" column, the "Second layer" column, the "Third layer" column, the "Fourth layer" column and the "Fifth layer (inner layer)" column in Table 1, the designation(s) of an ingredient or ingredients for each layer is shown in an upper line, and a mixing ratio (weight ratio) for a mixture of two or more ingredients is shown in a middle line. Further, the thickness of each layer is shown in a lower line. In Example 1, and Example 2 and Comparative Examples 1 to 3 to be described below, the first layer (outer layer) 1, the second layer (outer intermediate layer) 2, the third layer (middle layer) 3, the fourth layer (inner intermediate layer) 4 and the fifth layer (inner layer) 5 had thicknesses of 20 μm, 85 μm, 20 μm, 25 μm and 30 μm, respectively.

Then, two multilayer films thus produced were stacked one on the other with their fifth layers 5 opposed to each other, whereby a container (multi-chamber bag) 10 having two container portions 13, 14 as shown in FIG. 4 was produced. Sealing conditions for formation of a peripheral edge portion (heavily sealed portion) 11 of the container 10 were a sealing temperature of 185° C. and a sealing period of 3 seconds, and sealing conditions for formation of a weakly sealed portion 12 were a sealing temperature of 146° C. and a sealing period of 3 seconds.

The container portion 13 of the container 10 had a maximum capacity of about 300 mL, and was filled with 150 mL of distilled water. On the other hand, the container portion 14 had a maximum capacity of about 500 mL, and was filled with 350 mL of distilled water.

Example 2 and Comparative Examples 1 to 3

Containers (multi-chamber bags) 10 were each produced in substantially the same manner as in Example 1, except that different ingredients were employed for formation of the respective layers of the multilayer films as shown in Table 1.

pulling rate of 200 mm/min), and a force (interlayer strength in the unit of N) required for separating the second layer and the third layer of the multilayer film from each other was determined. A measurement result was provided as an average of measurement values obtained for 5 test strips.

A multilayer film having an interlayer strength not less than 4.0 N was rated as excellent (A+), a multilayer film having an interlayer strength not less than 3.0 N and less than 4.0 N was rated as good (A), and a multilayer film having an interlayer strength not less than 2.4 N and less than 3.0 N was rated as

TABLE 1

|  | First layer (outer layer) | Second layer | Third layer | Fourth layer | Fifth layer (inner layer) |
|---|---|---|---|---|---|
| Example 1 | R-PP1 20 μm | R-PP1 + R-PP2 + α-OE1 (27.5:27.5:45) 85 μm | COP + PE (80:20) 20 μm | R-PP1 + R-PP2 + α-OE1 (27.5:27.5:45) 25 μm | H-PP + R-PP1 (80:20) 30 μm |
| Example 2 | H-PP 20 μm | R-PP1 + R-PP2 + α-OE1 (27.5:27.5:45) 85 μm | COP + PE (80:20) 20 μm | R-PP1 + R-PP2 + α-OE1 (27.5:27.5:45) 25 μm | H-PP + R-PP1 (80:20) 30 μm |
| Comparative Example 1 | R-PP1 20 μm | R-PP1 + R-PP2 + α-OE1 (27.5:27.5:45) 85 μm | R-PP1 20 μm | R-PP1 + R-PP2 + α-OE1 (27.5:27.5:45) 25 μm | H-PP + R-PP1 (80:20) 30 μm |
| Comparative Example 2 | R-PP1 20 μm | R-PP1 + R-PP2 + α-OE1 (27.5:27.5:45) 85 μm | COP 20 μm | R-PP1 + R-PP2 + α-OE1 (27.5:27.5:45) 25 μm | H-PP + R-PP1 (80:20) 30 μm |
| Comparative Example 3 | R-PP1 20 μm | R-PP1 + R-PP2 (50:50) 85 μm | COP 20 μm | R-PP1 + R-PP2 (50:50) 25 μm | H-PP + R-PP1 (80:20) 30 μm |

Property Evaluation

The multilayer films and the containers (multi-chamber bags) 10 obtained in Examples 1 and 2 and Comparative Examples 1 to 3 were evaluated for the following properties.

(1) Transparency

A plurality of containers (multi-chamber bags) were prepared for each of Examples 1 to 2 and Comparative Examples 1 to 3, and the containers 10 were subjected to a high-pressure steam sterilization process at 121° C. for 20 minutes.

Then, test samples were cut out of each of the multilayer films of the containers 10 subjected to the high-pressure steam sterilization process, and the light transmittance of each of the test samples was measured at a wavelength of 450 nm in water. Six test samples per container 10 were made for three containers (total 18). A measurement result was provided as an average of measurement values obtained for 18 test samples.

The transparency of each of the containers (multi-chamber bags) 10 was determined after the container 10 was subjected to a high-pressure steam sterilization process. A container having a light transmittance not less than 90% was rated as excellent (A+), and a container having a light transmittance not less than 85% and less than 90% was rated as good (A). A container having a light transmittance not less than 80% and less than 85% was rated as unsatisfactory (B), and a container having a light transmittance less than 80% was rated as unacceptable (C).

(2) Interlayer Strength

Test strips each having a width of 15 mm were cut out of each of the multilayer films obtained in Examples 1 and 2 and Comparative Examples 1 to 3. Then, the test strips were each incised at a part of an interface between the second layer (outer intermediate layer) 2 and the third layer (middle layer) 3 thereof perpendicularly to the width thereof (longitudinally thereof). Subsequently, at the incised portion, a laminate of the first layer 1 and the second layer 2 and a laminate of the third to fifth layers 3 to 5 were clamped by a tensile tester and pulled away from each other at an angle of 90 degrees (at a fair (A–). A multilayer film having an interlayer strength not less than 2.0 N and less than 2.4 N was rated as unsatisfactory (B), and a multilayer film having an interlayer strength less than 2.0 N was rated as unacceptable (C).

(3) Plate Drop Strength

Rectangular bags each having a width of 130 mm and a length of 250 mm and having a 5-mm wide peripheral sealed portion provided on four lateral sides thereof were each produced as a sample by employing two multilayer films obtained in each of Examples 1 and 2 and Comparative Examples 1 to 3. About 500 mL of distilled water was filled in each of the rectangular bags.

The rectangular bag was placed on a flat work table in a 5° C. atmosphere, and an iron plate (30 cm (width)×32 cm (length)) having a weight of 6.4 kg was dropped onto the rectangular bag from the above with its attitude kept horizontal. The iron plate was dropped from different heights, and an iron plate dropping height (cm) for which breakage of the rectangular bag was observed was determined and employed as the plate drop strength. A measurement result was provided as an average of measurement values obtained for 10 samples.

A bag having a plate drop strength (height) not less than 10 cm was rated as good (A), and a bag having a plate drop strength (height) not less than 5 cm and less than 10 cm was rated as unsatisfactory (B). A bag having a plate drop strength (height) less than 5 cm was rated as unacceptable (C).

(4) Unsealability

In the production of the containers 10, different heat-sealing temperatures in 1° C. increments were employed for the formation of the weakly sealed portions 12. The weakly sealed portion 12 of each of the resulting containers 10 was unsealed for evaluation of the unsealability.

A container having excellent unsealability in all the weakly sealed portions 12 respectively formed at heat-sealing temperatures of 145 to 147° C. was rated as good (A), and a container having unsatisfactory unsealability in at least one of the weakly sealed portions 12 respectively formed at the heat-sealing temperatures was rated as unacceptable (C).

(5) Heat Resistance

Rectangular bags produced in the same manner as those used for the measurement of the plate drop strength (and filled with about 500 mL of distilled water) were subjected to a high-pressure steam sterilization process at 121° C. for 20 minutes. After the high-pressure steam sterilization process, the rectangular bags were each visually checked for deformation, breakage and unsealing. Based on the results of the check, the multilayer films were each evaluated for heat resistance on the basis of the following criteria.

A (good): None of deformation, breakage and unsealing was observed, or neither breakage nor unsealing was observed but slight evidence of deformation was observed. In either case, the heat resistance was regarded to be good.

C (unacceptable): Evidence of deformation was observed, and breakage or unsealing was also observed.

(6) Contamination Resistance

Rectangular bags produced in the same manner as those used for the measurement of the plate drop strength (and filled with about 500 mL of distilled water) were subjected to a high-pressure steam sterilization process at 121° C. for 20 minutes. After the high-pressure steam sterilization process, components contained in the distilled water in each of the rectangular bags were analyzed by gas chromatography. Thus, the rectangular bag was checked for exudation of additives contained in a resin of the multilayer film.

Examples of the additives contained in the resin of the multilayer film include an anti-oxidant, an anti-blocking agent and a lubricant.

Where the exudation of the additives was not observed (the total concentration of the additives in the distilled water was less than 1 ppm) as a result of the analysis, the contamination resistance was regarded to be excellent (A). Where the total concentration of the additives in the distilled water was not less than 1 ppm, the contamination resistance was regarded to be unacceptable (C).

The results of the property evaluation are shown in Table 2.

tive Example 2 in which the third layer was formed of the polycycloolefin alone was inferior in mechanical strength (interlayer strength and plate drop strength). Comparative Example 3 in which the third layer was formed of the polycycloolefin alone and the second and fourth layers contained no α-olefin elastomer was much inferior in mechanical strength (interlayer strength and plate drop strength).

Production of Multilayer Films and Containers

Example 3

A multilayer film having a layered structure as shown in FIG. 1 and a thickness of 180 μm was produced by a water-cooling co-extrusion inflation method. Ingredients for the respective layers are shown in Table 3. In the "First layer (outer layer)" column, the "Second layer" column, the "Third layer" column, the "Fourth layer" column and the "Fifth layer (inner layer)" column in Table 3, the designation(s) of an ingredient or ingredients for each layer is shown in an upper line, and a mixing ratio (weight ratio) for a mixture of two or more ingredients is shown in a middle line. Further, the thickness of each layer is shown in a lower line.

Then, two multilayer films thus produced were stacked one on the other with their fifth layers 5 opposed to each other, whereby a container (multi-chamber bag) 10 having two container portions 13, 14 as shown in FIG. 4 was produced. Sealing conditions for formation of a peripheral edge portion (heavily sealed portion) 11 of the container 10 were a sealing temperature of 185° C. and a sealing period of 3 seconds, and sealing conditions for formation of a weakly sealed portion 12 were a sealing temperature of 146° C. and a sealing period of 3 seconds.

The container portion 13 of the container 10 had a maximum capacity of about 300 mL, and was filled with 150 mL

TABLE 2

| | (1) Transparency | (2) Interlayer strength | (3) Plate drop strength | (4) Unsealability | (5) Heat resistance | (6) Contamination resistance |
| --- | --- | --- | --- | --- | --- | --- |
| Example 1 | 92.5% | 4.41 N | 11.0 cm | A | A | A |
| | A+ | A+ | A | | | |
| Example 2 | 91.7% | 4.41 N | 10.5 cm | A | A | A |
| | A+ | A+ | A | | | |
| Comparative Example 1 | 95.7% | 4.41 N | 17.5 cm | A | A | C |
| | A+ | A+ | A | | | |
| Comparative Example 2 | 93.4% | 2.94 N | 6.7 cm | A | A | A |
| | A+ | A− | B | | | |
| Comparative Example 3 | 94.3% | 1.47 N | 4.0 cm | A | A | A |
| | A+ | C | C | | | |

As shown in Table 2, the multilayer films and the containers of Examples 1 and 2 were excellent in transparency, mechanical strength (interlayer strength and plate drop strength), weakly sealed portion unsealability, heat resistance and contamination resistance (the effect of suppressing the exudation).

In contrast, Comparative Example 1 in which the third layer was formed of the propylene-ethylene random copolymer was inferior in contamination resistance, and Comparaof distilled water. On the other hand, the container portion 14 had a maximum capacity of about 500 mL, and was filled with 350 mL of distilled water.

Examples 4 and 5 and Comparative Examples 4 to 6

Containers (multi-chamber bags) 10 were each produced in substantially the same manner as in Example 3, except that different ingredients were employed for the respective layers of the multilayer films as shown in Table 3.

TABLE 3

|  | First layer (outer layer) | Second layer | Third layer | Fourth layer | Fifth layer (inner layer) |
|---|---|---|---|---|---|
| Example 3 | R-PP1 20 μm | R-PP1 + R-PP2 + α-OE1 (27.5:27.5:45) 85 μm | COP + PE (80:20) 20 μm | R-PP1 + R-PP2 + α-OE1 (27.5:27.5:45) 25 μm | H-PP + R-PP1 (82.5:17.5) 30 μm |
| Example 4 | R-PP1 20 μm | R-PP1 + R-PP2 + α-OE1 (27.5:27.5:45) 95 μm | COP + PE (80:20) 10 μm | R-PP1 + R-PP2 + α-OE1 (27.5:27.5:45) 25 μm | H-PP + R-PP1 (82.5:17.5) 30 μm |
| Example 5 | R-PP1 20 μm | R-PP1 + R-PP2 + α-OE1 (27.5:27.5:45) 85 μm | COP + PE (60:40) 20 μm | R-PP1 + R-PP2 + α-OE1 (27.5:27.5:45) 25 μm | H-PP + R-PP1 (82.5:17.5) 30 μm |
| Comparative Example 4 | R-PP1 20 μm | R-PP1 + R-PP2 + α-OE1 (27.5:27.5:45) 85 μm | COP + α-OE2 (80:20) 20 μm | R-PP1 + R-PP2 + α-OE1 (27.5:27.5:45) 25 μm | H-PP + R-PP1 (82.5:17.5) 30 μm |
| Comparative Example 5 | R-PP1 20 μm | R-PP1 + R-PP2 + α-OE1 (27.5:27.5:45) 85 μm | COP + R-PP1 (80:20) 20 μm | R-PP1 + R-PP2 + α-OE1 (27.5:27.5:45) 25 μm | H-PP + R-PP1 (82.5:17.5) 30 μm |
| Comparative Example 6 | R-PP1 20 μm | R-PP1 + R-PP2 + α-OE1 (27.5:27.5:45) 85 μm | COP 20 μm | R-PP1 + R-PP2 + α-OE1 (27.5:27.5:45) 25 μm | H-PP + R-PP1 (82.5:17.5) 30 μm |

Property Evaluation

The multilayer films and the containers (multi-chamber bags) 10 obtained in Examples 3 to 5 and Comparative Examples 4 to 6 were evaluated for the following properties.

(1) Transparency

A plurality of containers (multi-chamber bags) 10 were prepared for each of Examples 3 to 5 and Comparative Examples 4 to 6, and some of the containers 10 were subjected to a high-pressure steam sterilization process at 121° C. for 20 minutes.

Then, test samples were cut out of each of the multilayer films of the containers 10 not subjected to the high-pressure steam sterilization process and the containers 10 subjected to the high-pressure steam sterilization process, and the light transmittance of each of the test samples was measured at a wavelength of 450 nm in water. Six test samples per container 10 were made for three containers (total 18). A measurement result was provided as an average of measurement values obtained for 18 test samples of each of the containers not subjected to the high-pressure steam sterilization process and the containers subjected to the high-pressure steam sterilization process.

The containers (multi-chamber bags) 10 were each evaluated for transparency before and after the high-pressure steam sterilization process on the basis of the criteria of Example 1.

(2) Interlayer Strength

Test strips each having a width of 15 mm were cut out of each of the multilayer films obtained in Examples 3 to 5 and Comparative Examples 3 to 6. Then, a force (interlayer strength in the unit of N) required for separating the second layer (outer intermediate layer) 2 and the third layer (middle layer) 3 of the multilayer film from each other was determined in the manner in Example 1. A measurement result was provided as an average of measurement values obtained for 5 test strips.

The interlayer films were each evaluated for interlayer strength on the basis of the criteria of Example 1.

(3) Plate Drop Strength

Rectangular bags were each produced by employing two multilayer films obtained in each of Examples 3 to 5 and Comparative Examples 4 to 6. Then, the plate drop strength (plate dropping height in the unit of cm) for which breakage of the rectangular bag was observed was determined in the manner of Example 1.

The rectangular bags (containers) were each evaluated for plate drop strength on the basis of the criteria of Example 1.

The results of the property evaluation are shown in Table 4.

TABLE 4

|  | (1) Transparency | | (2) | (3) |
|---|---|---|---|---|
|  | Before sterilization | After sterilization | Interlayer strength | Plate drop strength |
| Example 3 | 96.1% A+ | 92.2% A+ | 4.41 N A+ | 11.7 cm A |
| Example 4 | 96.8% A+ | 95.0% A+ | 3.33 N A | 15.0 cm A |
| Example 5 | 96.3% A+ | 90.7% A+ | 2.45 N A− | 15.0 cm A |
| Comparative Example 4 | 87.6% A | 81.3% B | 3.14 N A | 13.3 cm A |
| Comparative Example 5 | 82.5% B | 83.5% B | 2.45 N A− | 13.3 cm A |
| Comparative Example 6 | 97.4% A+ | 93.4% A+ | 2.94 N A− | 6.7 cm B |

As shown in Table 4, the multilayer films and the containers of Examples 3 to 5 were excellent in transparency and mechanical strength (interlayer strength and plate drop strength).

On the other hand, Comparative Example 4 in which the third layer was composed of a mixture of the polycycloolefin and the α-olefin elastomer and Comparative Example 5 in which the third layer was composed of a mixture of the polycycloolefin and the propylene-ethylene random copolymer were inferior in transparency and interlayer strength. Further, Comparative Example 6 in which the third layer was composed of the polycycloolefin alone was inferior in plate drop strength.

Production of Multilayer Films and Containers

Examples 6 to 10

Multilayer films each having a layered structure as shown in FIG. 1 were produced by a water-cooling co-extrusion inflation method. Ingredients for the respective layers are shown in Table 5. In the "First layer (outer layer)" column, the "Second layer" column, the "Third layer" column, the "Fourth layer" column and the "Fifth layer (inner layer)" column in Table 5, the designation(s) of an ingredient or ingredients for each layer is shown in an upper line, and a mixing ratio (weight ratio) for a mixture of two or more ingredients is shown in a middle line. Further, the thickness of each layer is shown in a lower line.

Then, two multilayer films thus produced were stacked one on the other with their fifth layers 5 opposed to each other, whereby a container (multi-chamber bag) 10 having two container portions 13, 14 as shown in FIG. 4 was produced. Sealing conditions for formation of a peripheral edge portion (heavily sealed portion) 11 of the container 10 were a sealing temperature of 185° C. and a sealing period of 3 seconds, and sealing conditions for formation of a weakly sealed portion 12 were a sealing temperature of 146° C. and a sealing period of 3 seconds.

The container portion 13 of the container 10 had a maximum capacity of about 300 mL, and was filled with 150 mL of distilled water. On the other hand, the container portion 14 had a maximum capacity of about 500 mL, and was filled with 350 mL of distilled water.

The interlayer films were each evaluated for interlayer strength on the basis of the aforementioned criteria.

(3) Drop Test

Rectangular bags each having a width of 130 mm and a length of 250 mm and having a 5-mm wide peripheral sealed portion provided on four lateral sides thereof were each produced by employing two multilayer films obtained in each of Examples 1 and 6 to 10. Then, about 500 mL of distilled water was filled in each of the rectangular bags.

Then, ten such rectangular bags were stored in a 0° C. atmosphere for two days, and thereafter dropped in a stacked state from a height of 1.2 m with their attitudes kept horizontal. This dropping operation was repeatedly performed, and the number of times of the dropping operation performed until breakage of the rectangular bags was observed was determined.

TABLE 5

|  | First layer (outer layer) | Second layer | Third layer | Fourth layer | Fifth layer (inner layer) |
|---|---|---|---|---|---|
| Example 1 | R-PP1 20 μm | R-PP1 + R-PP2 + α-OE1 (27.5:27.5:45) 85 μm | COP + PE (80:20) 20 μm | R-PP1 + R-PP2 + α-OE1 (27.5:27.5:45) 25 μm | H-PP + R-PP1 (80:20) 30 μm |
| Example 6 | R-PP1 20 μm | R-PP1 + R-PP2 + α-OE1 (27.5:27.5:45) 55 μm | COP + PE (80:20) 20 μm | R-PP1 + R-PP2 + α-OE1 (27.5:27.5:45) 55 μm | H-PP + R-PP1 (80:20) 30 μm |
| Example 7 | R-PP1 20 μm | R-PP1 + R-PP2 + α-OE1 (27.5:27.5:45) 65 μm | COP + PE (80:20) 20 μm | R-PP1 + R-PP2 + α-OE1 (27.5:27.5:45) 65 μm | H-PP + R-PP1 (80:20) 30 μm |
| Example 8 | R-PP1 20 μm | R-PP1 + R-PP2 + α-OE1 (27.5:27.5:45) 65 μm | COP + PE (80:20) 15 μm | R-PP1 + R-PP2 + α-OE1 (27.5:27.5:45) 65 μm | H-PP + R-PP1 (80:20) 30 μm |
| Example 9 | R-PP1 20 μm | R-PP1 + R-PP2 + α-OE1 (27.5:27.5:45) 65 μm | COP + PE (80:20) 20 μm | R-PP1 + R-PP2 + α-OE1 (27.5:27.5:45) 65 μm | H-PP + R-PP1 (70:30) 30 μm |
| Example 10 | R-PP1 20 μm | R-PP1 + R-PP2 + α-OE1 (27.5:27.5:45) 65 μm | COP + PE (80:20) 20 μm | R-PP1 + R-PP2 + α-OE1 (27.5:27.5:45) 65 μm | H-PP + R-PP1 (60:40) 30 μm |

Property Evaluation

The multilayer films and the containers (multi-chamber bags) 10 obtained in Examples 1 and 6 to 10 were evaluated for the following properties.

(1) Transparency

A plurality of containers (multi-chamber bags) 10 were prepared for each of Examples 1 and 6 to 10, and the containers 1 and 6 to 10 were subjected to a high-pressure steam sterilization process at 123° C. for 13 minutes.

Then, test samples were cut out of each of the multilayer films of the containers 10 subjected to the high-pressure steam sterilization process, and the light transmittance of each of the test samples was measured at a wavelength of 450 nm in water. Six test samples per container 10 were made for three containers (total 18). A measurement result was provided as an average of measurement values obtained for 18 test samples.

The containers (multi-chamber bags) 10 were each evaluated for transparency on the basis of the criteria of Example 1.

(2) Interlayer Strength

Test strips each having a width of 15 mm were cut out of each of the multilayer films obtained in Examples 1 and 6 to 10. Then, a force (interlayer strength in the unit of N) required for separating the second layer (outer intermediate layer) 2 and the (middle layer) 3 of the multilayer film from each other was determined in the aforementioned manner. A measurement result was provided as an average of measurement values obtained for 5 test strips.

It is more advantageous that the number of times of the dropping operation performed until the breakage of the rectangular bags is greater. The number of times of the dropping operation is preferably not less than 5, more preferably not less than 10 for practical use.

The results of the evaluation are shown in Table 6.

TABLE 6

|  | (1) Transparency | (2) Interlayer strength | (3) Drop test (times) |
|---|---|---|---|
| Example 1 | 89% A | 2.80 N A− | 6.3 |
| Example 6 | 87% A | 4.38 N A+ | 10 or more |
| Example 7 | 88% A | 4.34 N A+ | 10 or more |
| Example 8 | 88% A | 4.37 N A+ | 10 or more |
| Example 9 | 85% A | 4.32 N A+ | 10 or more |
| Example 10 | 85% A | 4.43 N A+ | 10 or more |

As shown in Table 6, the multilayer films and the containers of Examples 6 to 10 were excellent in transparency similarly to that of Example 1. Further, Examples 6 to 10 are superior to Example 1 in interlayer strength and drop test.

While the present invention has been provided by way of exemplary embodiments thereof, these embodiments are merely illustrative but not limitative of the invention. It should be understood that modifications of the present invention apparent to those skilled in the art fall within the scope of the invention defined by the appended claims.

INDUSTRIAL APPLICABILITY

The inventive multilayer film is suitable, for example, as a material for containers and, particularly, as a material for medical containers such as infusion solution bags. The inventive container is suitable, for example, as a medical container such as an infusion solution bag.

The invention claimed is:

1. A multilayer film comprising:
   a first layer;
   a second layer provided on the first layer;
   a third layer provided on the second layer;
   a fourth layer provided on the third layer; and
   a fifth layer provided on the fourth layer;
   wherein
   the first layer comprises a propylene-ethylene random copolymer having a melt flow rate not less than 0.5 g/10 minutes and not greater than 10 g/10 minutes as measured at 230° C.;
   the second layer and the fourth layer each comprise a mixture of a propylene-ethylene random copolymer and an α-olefin elastomer;
   the third layer comprises a mixture of a polycycloolefin and a polyethylene; and
   the fifth layer comprises a mixture containing a polypropylene homopolymer having a melt flow rate not less than 0.5 g/10 minutes and not greater than 5 g/10 minutes as measured at 230° C. and a propylene-ethylene random copolymer having a melt flow rate not less than 0.5 g/10 minutes and not greater than 10 g/10 minutes as measured at 230° C. in a weight ratio of 90:10 to 10:90 and;
   the propylene-ethylene random copolymer in the second layer and the fourth layer is a mixture of a low-MFR propylene-ethylene random copolymer having a melt flow rate not less than 0.5 g/10 minutes and less than 5 g/10 minutes as measured at 230° C. and a high-MFR propylene-ethylene random copolymer having a melt flow rate not less than 5 g/10 minutes and not greater than 10 g/10 minutes as measured at 230° C.

2. The multilayer film according to claim 1, wherein the mixture for the third layer contains the polycycloolefin in a proportion of 50 to 95% by weight based on the total weight thereof.

3. The multilayer film according to claim 1, wherein the mixture for the second layer and the fourth layer contains the α-olefin elastomer in a proportion of 30 to 60% by weight based on the total weight thereof.

4. The multilayer film according to claim 1, wherein a thickness of the second layer is not less than 0.8 times a thickness of the fourth layer.

5. The multilayer film according to claim 4, wherein the thickness of the second layer is not greater than 1.2 times the thickness of the fourth layer.

6. The multilayer film according to claim 1, wherein a total thickness of the second layer and the fourth layer is not less than 50% of a thickness of the multilayer film.

7. A container formed of a multilayer film including a first layer, a second layer provided on the first layer, a third layer provided on the second layer, a fourth layer provided on the third layer, and a fifth layer provided on the fourth layer, wherein
   the first layer comprises a propylene-ethylene random copolymer having a melt flow rate not less than 0.5 g/10 minutes and not greater than 10 g/10 minutes as measured at 230° C.,
   the second layer and the fourth layer each comprise a mixture of a propylene-ethylene random copolymer and an α-olefin elastomer,
   the third layer comprises a mixture of a polycycloolefin and a polyethylene,
   the fifth layer comprises a mixture containing a polypropylene homopolymer having a melt flow rate not less than 0.5 g/10 minutes and not greater than 5 g/10 minutes as measured at 230° C. and a propylene-ethylene random copolymer having a melt flow rate not less than 0.5 g/10 minutes and not greater than 10 g/10 minutes as measured at 230° C. in a weight ratio of 90:10 to 10:90,
   the propylene-ethylene random copolymer contained in the second layer and the fourth layer is a mixture of a low-MFR propylene-ethylene random copolymer having a melt flow rate not less than 0.5 g/10 minutes and less than 5 g/10 minutes as measured at 230° C. and a high-MFR propylene-ethylene random copolymer having a melt flow rate not less than 5 g/10 minutes and not greater than 10 g/10 minutes as measured at 230° C., and
   the first layer and the fifth layer respectively serve as an outer layer and an inner layer of the container.

* * * * *

UNITED STATES PATENT AND TRADEMARK OFFICE
CERTIFICATE OF CORRECTION

PATENT NO.       : 8,784,958 B2
APPLICATION NO.  : 12/528305
DATED            : July 22, 2014
INVENTOR(S)      : Fujio Inoue et al.

It is certified that error appears in the above-identified patent and that said Letters Patent is hereby corrected as shown below:

In the Claims

In claim 1, column 23, line 24, "230° C.;" should read --230°C;--.

In claim 1, column 23, line 33, "230° C." should read --230°C--.

In claim 1, column 23, line 36, "230° C." should read --230°C--.

In claim 1, column 23, line 42, "230° C." should read --230°C--.

In claim 1, column 23, line 45, "230° C." should read --230°C.--.

In claim 7, column 24, line 24, "230° C.," should read --230°C,--.

In claim 7, column 24, line 34, "230° C." should read --230°C--.

In claim 7, column 24, line 37, "230° C." should read --230°C--.

In claim 7, column 24, line 42, "230° C." should read --230°C--.

In claim 7, column 24, line 45, "230° C.," should read --230°C,--.

Signed and Sealed this
Thirtieth Day of December, 2014

Michelle K. Lee
*Deputy Director of the United States Patent and Trademark Office*